United States Patent [19]

Pasky

[11] 4,451,684
[45] May 29, 1984

[54] CO-OLIGOMERIZATION OF OLEFINS

[75] Inventor: Joseph Z. Pasky, Novato, Calif.

[73] Assignee: Chevron Research Company, San Francisco, Calif.

[21] Appl. No.: 402,490

[22] Filed: Jul. 27, 1982

[51] Int. Cl.$^3$ .............................................. C07C 3/02
[52] U.S. Cl. .................................. 585/329; 585/510; 585/525
[58] Field of Search ............... 585/329, 511, 512, 521, 585/522, 525, 510, 530, 532

[56] References Cited

U.S. PATENT DOCUMENTS

| | | | |
|---|---|---|---|
| 4,172,855 | 10/1979 | Shubkin et al. | 585/511 |
| 4,263,465 | 4/1981 | Sheng et al. | 585/329 |
| 4,300,006 | 11/1981 | Nelson | 585/329 |
| 4,317,948 | 3/1982 | Heckelsberg | 585/329 |
| 4,319,064 | 3/1982 | Heckelsberg et al. | 585/329 |

FOREIGN PATENT DOCUMENTS 576759  5/1959  Canada .............................. 585/511

*Primary Examiner*—Patrick Garvin
*Assistant Examiner*—A. Pal
*Attorney, Agent, or Firm*—S. R. La Paglia; T. G. De Jonghe; C. J. Caroli

[57] ABSTRACT

Preparation of $C_{20}$–$C_{40}$ branched-chain olefins by the co-oligomerization of $C_{12}$–$C_{18}$ branched-chain internal olefins with $C_5$'$C_6$ olefins by a process comprising (a) contacting a propylene oligomer feedstock having from 12 to 18 carbon atoms with a $C_5$–$C_6$ olefin feedstock in a reaction zone in the presence of a boron trifluoride-alkanol catalyst; (b) maintaining the temperature in the reaction zone between about 0° C. and 80° C.; and (c) maintaining the pressure in the reaction zone between about 0 psig and 200 psig.

5 Claims, No Drawings

CO-OLIGOMERIZATION OF OLEFINS

BACKGROUND OF THE INVENTION

The present invention relates to a process for the preparation of $C_{20}$–$C_{40}$ branched-chain olefins by the co-oligomerization of $C_{12}$–$C_{18}$ branched-chain internal olefins with $C_5$–$C_6$ olefins in the presence of a boron trifluoride-alkanol catalyst.

The oligomerization of alpha olefins is well known in the art. Thus, U.S. Pat. No. 3,932,553 describes the oligomerization of propylene in the presence of a boron trifluoride catalyst and a small amount of an olefinic diene to provide oligomers having about 15 to 21 carbon atoms.

U.S. Pat. No. 4,024,203 describes the oligomerization of lower molecular weight mono alpha olefins utilizing a catalyst composition containing a Bronsted acid, a sulfone, and optionally, a Lewis acid, to provide predominantly dimers and trimers.

U.S. Pat. No. 4,041,098 describes a method of oligomerizing straight-chain alpha olefins having from 3 to 14 carbon atoms with a soluble catalyst system consisting of an aluminum alkyl halide and an organo halide.

U.S. Pat. Nos. 4,045,507 and 4,045,508 describe the oligomerization of alpha olefins having about 5 to 14 carbon atoms, particularly 1-decene and mixtures of 1-decene with 1-octene and/or 1-dodecene, in the presence of a boron trifluoride catalyst and a co-catalyst that complexes with boron trifluoride to provide an oligomer mixture including trimer and tetramer.

SUMMARY OF THE INVENTION

It has now been found that the production of $C_{20}$–$C_{40}$ branched-chain olefins is successfully achieved by the co-oligomerization of $C_{12}$–$C_{18}$ branched-chain internal olefins with $C_5$–$C_6$ olefins by a process which comprises (a) contacting a propylene oligomer feedstock having from 12 to 18 carbon atoms with a $C_5$–$C_6$ olefin feedstock in a reaction zone in the presence of a boron trifluoridealkanol catalyst; (b) maintaining the temperature in the reaction zone between about 0° C. and 80° C.; and (c) maintaining the pressure in the reaction zone between about 0 psig and 200 psig.

Among other factors, the present invention is based on the discovery that $C_{12}$–$C_{18}$ internal olefins which are also highly branched can be co-oligomerized with $C_5$–$C_6$ olefins to provide high molecular weight branched-chain olefins in high yield and conversions.

The process of the present invention is suitable for the production of $C_{20}$–$C_{40}$ branched-chain olefins. The olefins thus prepared are highly branched compounds and the term "branched-chain" is herein used to signify at least one carbon branch per every 5 carbon atoms in the olefin product.

A propylene oligomer feedstock having from 12 to 18 carbon atoms and an internal double bond is used as a starting material. This feedstock may be obtained by the direct oligomerization of propylene in an acid medium.

The propylene oligomer feedstock is contacted with a $C_5$–$C_6$ olefin feedstock in the presence of a boron trifluoride-alkanol catalyst. The $C_5$–$C_6$ olefin may be obtained as a product of naphtha cracking and normally will contain a mixture of both straight-chain and branched-chain olefins. The reaction is carried out at a temperature of about 0° C. to about 80° C., preferably from about 10° C. to about 60° C. The reaction pressure is maintained at about 0 psig to about 200 psig, preferably from about 0 psig to about 150 psig.

The use of boron trifluoride-alkanol as the co-oligomerization catalyst has been found to be satisfactory for providing the olefin product in high yield.

The boron trifluoride catalyst is preferably utilized in combination with an alkanol. Suitable alkanols include straight-chain alkanols of 1 to 8 carbon atoms. A preferred alkanol is normal butanol. Generally, about 0.01 to 1, and preferably about 0.05 to 0.5, moles of boron trifluoride are utilized per mole of olefin feedstock. The boron trifluoride-alkanol catalyzed reaction proceeds to give over 40% conversion to the olefin product.

The co-oligomerized branched-chain olefinic products may be separated from the reaction mixture by conventional procedures, such as fractional distillation.

The $C_{20}$–$C_{40}$ branched-chain olefins prepared by the process of the present invention are useful as precursors for surface-active products, lubricating compositions, and the like.

The following example is provided to illustrate the invention in accordance with the principles of the invention but is not to be construed as limiting the invention in any way except as indicated by the appended claims.

EXAMPLE

Example 1

A 2-liter, 3-necked, round-bottom flask was equipped with a boron trifluoride bubbler, stirrer, dropping funnel, thermometer and condenser with ice trap and drierite tube. To this flask, 660 ml (2.6 moles) of a propylene polymer having an average molecular weight of about 200 and 960 ml (12.5 moles) of $C_5$+$C_6$ distilled FCC light gasoline was added and saturated with boron trifluoride. With stirring, 120 ml (1.6 moles) of n-butanol was added over a period of 180 minutes, while maintaining a temperature of 40° C. The reaction was run for 6 hours and the results are shown in Table 1.

TABLE 1

| Time, hours | Olefin Conversion |
| --- | --- |
| 1 | — |
| 2 | 4% |
| 3 | 25% |
| 4 | 31% |
| 5 | 36% |
| 6 | 44% |

What is claimed is:

1. A process for the preparation of $C_{20}$–$C_{40}$ branched-chain olefins by the co-oligomerization of a propylene oligomer feedstock having from 12 to 18 carbon atoms with $C_5$–$C_6$ olefins which comprises:
    (a) contacting the propylene oligomer feedstock having from 12 to 18 carbon atoms with a $C_5$–$C_6$ olefin feedstock in a reaction zone in the presence of a boron trifluoride-alkanol catalyst;
    (b) maintaining the temperature in the reaction zone between about 0° C. and 80° C.; and
    (c) maintaining the pressure in the reaction zone between about 0 psig and 200 psig.

2. A process according to claim 1, wherein the alkanol is normal butanol.

3. A process according to claim 1, wherein the reaction is carried out at a temperature between about 10° C. and 60° C.

4. A process according to claim 1, wherein the reaction is carried out at a pressure between about 0 psig and 150 psig.

5. A process according to claim 1, wherein the reaction zone reaction conditions are maintained sufficient to yield at least 40% conversion of the olefin feedstock to the $C_{20}$–$C_{40}$ branched-chain olefins, including a temperature between about 0° C. and 80° C., and a pressure between about 0 psig and 200 psig.

* * * * *